United States Patent [19]

Wong et al.

[11] Patent Number: 5,508,172
[45] Date of Patent: Apr. 16, 1996

[54] MODIFIED SOY FIBER MATERIAL OF IMPROVED SENSORY PROPERTIES

[75] Inventors: Theodore M. Wong, Manchester; David A. Singer, St. Louis; Santa H. C. Lin, Chesterfield, all of Mo.

[73] Assignee: Ralston Purina Company, St. Louis, Mo.

[21] Appl. No.: 443,096

[22] Filed: May 17, 1995

Related U.S. Application Data

[63] Continuation of Ser. No. 959,960, Oct. 13, 1992, abandoned.

[51] Int. Cl.$^6$ .................. C12Q 1/34; A23L 1/20
[52] U.S. Cl. .................. 435/18; 426/46; 426/52; 426/634
[58] Field of Search .................. 435/18; 426/46, 426/52, 634

[56] References Cited

U.S. PATENT DOCUMENTS

| | | | |
|---|---|---|---|
| 3,640,723 | 2/1972 | Uhlig et al. | 426/46 |
| 4,119,733 | 10/1978 | Hsieh | 426/46 |
| 4,478,940 | 10/1984 | Alder-Nissen et al. | 435/209 |
| 4,483,874 | 11/1984 | Olsen | 426/44 |
| 4,563,357 | 1/1986 | Witt | 426/46 |
| 4,619,831 | 10/1986 | Sharma | 426/93 |
| 4,784,860 | 11/1988 | Christensen | 426/46 |
| 5,100,679 | 3/1992 | Delrue | 426/44 |

FOREIGN PATENT DOCUMENTS

| | | |
|---|---|---|
| 1004535 | 2/1977 | Canada. |
| 90/10392 | 9/1990 | WIPO. |

OTHER PUBLICATIONS

"Improvement of the Sensory Properties of Two Different Dietary Fibre Sources through Enzymatic Modification", Caprez et al., Lebensmittel-Wiessenchaft and Technologies, vol. 20, pp. 245–250, 1987.

*Primary Examiner*—Ralph J. Gitomer
*Attorney, Agent, or Firm*—Richard B. Taylor

[57] ABSTRACT

The present invention relates to an enzymatically modified dietary fiber material particularly a soy fiber material of improved sensory properties including smoothness and mouthfeel characteristics. The modified fiber is formed by forming an aqueous slurry of a soy dietary fiber material and modifying or hydrolyzing the material with a process modifying dietary soy fiber and the resulting enzyme mixture which comprises a mixture of a cellulase and a carbohydrase. The degree of hydrolysis is sufficient to improve the sensory properties of the soy fiber material without substantially reducing the dietary fiber content thereof.

24 Claims, No Drawings

MODIFIED SOY FIBER MATERIAL OF IMPROVED SENSORY PROPERTIES

This is a continuation of application Ser. No. 07/959,960 filed on Oct. 13, 1992, now abandoned.

BACKGROUND OF THE INVENTION

The present invention relates to an enzymatically modified fiber material preferably a modified soy fiber material and process for the production thereof.

Dietary fiber has been recognized as an essential nutrient in the human diet so as a consequence a variety of food products include a dietary fiber material as an added ingredient. U.S. Pat. No. 4,976,982 for example describes a low calorie pasta product containing added fiber. U.S. Pat. No. 4,834,990 describes a non-dairy liquid food product made by adding dietary fiber and calcium to fruit juice and U.S. Pat. No. 4,959,227 describes a food product prepared from an aqueous composition containing non-fat milk solids and fiber. Additionally, U.S. Pat. No. 5,021,245 describes an infant formula containing a soy fiber material.

The most difficult type of food product in which to include a dietary fiber material particularly a soy fiber as an ingredient is a liquid material, particularly one of a relatively low viscosity. The added fiber material tends to resist suspension in the liquid matrix and introduces a gritty and chalky mouthfeel. Although a variety of techniques to overcome this problem have been proposed, including the coating of the fiber material with soluble fibers to improve smoothness as described in U.S. Pat. Nos. 4,565,702 and 4,619,831, for the most part, these represent expensive and undesirable alternatives.

A publication by Caprez et al entitled "Improvement of the Sensory Properties of Two Different Fibre Sources through Enzymatic Modification" published in *Lebensmittel-wissenschaft and Technologies* 20, p. 245–250 (1987) describes an alternative approach in which the sensory properties of apple pomace and pea hulls were improved with the use of a cellulase and pectinase combination. This enzymatic combination and the conditions used would be ineffective, however to improve the sensory properties of a dietary soy fiber material.

It is therefore an object of the present invention to provide a soy dietary fiber material of improved sensory properties.

It is also an object of the present invention to provide a soy dietary fiber material of improved sensory properties including smoothness and mouthfeel characteristics to provide a suitable dietary fiber for use in a liquid product.

It is a further object of the present invention to improve the sensory properties including mouthfeel characteristics and smoothness of the soy dietary fiber material without a substantial reduction in the total dietary fiber content of the material.

These and other objects will hereafter be apparent are achieved in the present invention as set forth below.

SUMMARY OF THE INVENTION

The present invention involves a process for improving or modifying the sensory properties including the mouthfeel characteristics and smoothness of a soy dietary fiber material by employing a mixture of enzymes to modify or smooth the exposed surfaces of the soy dietary fiber material in order to produce a product with less grittiness and chalkiness. These improved functional characteristics improve the usefulness of the modified soy dietary fiber material in liquid products, since as noted the smoothness and mouthfeel characteristics of the fiber is extremely important in liquid products. The present process comprises forming an aqueous slurry of the soy dietary fiber material followed by the addition of an enzyme mixture which comprises a mixture of a cellulase and a carbohydrase preferably in a weight ratio of 25 to 50% of a cellulase and 50 to 75% of a carbohydrase. Modification of the soy dietary fiber material is carried out under specific conditions of pH, time and temperature in order to improve the sensory properties including the mouthfeel characteristics and smoothness of the material. Following modification or hydrolysis of the soy fiber material the enzyme is inactivated and the modified material is dewatered. The conditions of modification or hydrolysis of the material with the enzyme mixture are sufficient to modify the sensory properties including the mouthfeel characteristics and smoothness of the fiber material without a substantial reduction in the dietary fiber content. For purposes of the present invention modification or hydrolysis of the soy fiber material pursuant to the present process only reduces the total dietary fiber content of the material not more than about 10% by weight. This amount of modification is sufficient to smooth the surfaces of the soy fiber material in order to improve its mouthfeel, but without an undesirable substantial reduction in the total dietary fiber content.

DESCRIPTION OF THE PREFERRED EMBODIMENTS

The soy fiber material that is employed in the present invention comprises a mixture of various types of complex carbohydrates and cellulosic and hemicellulosic substances. These materials are principally cell wall structural components of the soybean cotyledons and are produced as a by product from the production of a soy protein isolate. The present invention is directed primarily to the production of modified soy fiber materials. It is equally applicable to other dietary fiber materials.

A soy fiber material has also been characterized as a soy polysaccharide material or as the alkali insoluble residue from the soy isolate process. In this regard, the typical procedure for the production of a soy isolate involves the dispersal of a starting material such as soy flakes in an aqueous medium. The pH of the medium is then adjusted to at least about 7 by the addition of an alkali. The soluble carbohydrate and protein components are then solubilized in the aqueous alkaline solution and following centrifugation, the insoluble residue is composed of the fibrous components of the soy flakes and the remaining insoluble carbohydrates. The insoluble solids are sometimes referred to as the "spent flake residue." The insoluble or "spent flake residue" is then subjected to a second extraction step to remove as much soluble carbohydrates and protein as possible. The aqueous extracts from the double extraction procedure are then combined for further processing which includes acid precipitation and isolation of the protein fraction from the aqueous medium. The insoluble solids may then be dried if desired to provide a soy dietary fiber material for use in the present invention although typically the insoluble residue is further processed in order to remove any extraneous material as described in British Patent No. 2,020,666. The soy fiber material has a typical analysis after drying of a total carbohydrate content of about 80% by weight, a protein content of about 10–18% by weight and an ash content of about 5% by weight. The dried and cleaned soy fiber material is then suitable for use in the present invention as described in more detail below.

The dietary fiber or soy fiber material used as the starting material in the present invention may either be in dried or undried form. The dietary fiber material is initially formed into an aqueous slurry with heated water, preferably at a temperature of about 120°–140° F. The slurry has a solids content of about 5.0 to 9.5% by weight and preferably about 6 to 9% by weight. Following formation of the aqueous slurry the pH is adjusted to an acidic level, generally in the range of about 3.0 to 5.0 and preferably about 3.75 to 4.25. The pH is adjusted with any edible acid preferably phosphoric acid.

Following pH adjustment of the slurry of the soy dietary fiber material the fiber is modified or hydrolyzed in order to improve the sensory properties including the smoothness or mouthfeel characteristics of the material. This is achieved by the addition of an enzyme mixture which comprises a mixture of a cellulase and carbohydrase, in a weight ratio of about 25 to 50% parts by weight of the cellulase and 50 to 75% by weight of the carbohydrase. The preferred level of the enzymes in the mixture is about 1 part by weight of the cellulase and 3 parts by weight of the carbohydrase. The cellulase that is preferred for use in the present invention is "Celluclast 1.5L" which is available from (Novo Nordisk Bioindustrials, Inc., Danbury, Conn.). This enzyme has an activity of 1500 NCU/g (Novo Cellulase Units per gram as measured by the procedure described in Novo's analytical method AF 187.2). Enzyme is generally obtained from fungi such as *Trichoderma longbrachiatum*.

The carbohydrase that is preferred for use in the present invention is "Viscozyme L" available from (Novo Nordisk Bioindustrials, Inc., Danbury, Conn.). The activity of this enzyme is typically about 120 FBG/ml (Fungal Beta glucanase units as measured by the procedure described in J. Biol. Chem. 153, p. 375 (1944)). This enzyme contains a wide range of carbohydrases, including arabinase, cellulase, beta glucanases, hemicellulase and xylanases and is generally derived from Aspergillus. This combination of enzymes is added to the slurry of soy dietary fiber material in an amount effective to modify or hydrolyze the soy fiber material to an extent necessary to improve the sensory properties including the smoothness or mouthfeel characteristics of the material. Preferred amounts of the enzyme mixture is about 50 to 75% by weight of the solids content of the slurry.

After addition of the enzyme mixture the soy fiber material is hydrolyzed or modified for a period of time and at a temperature effective to smooth the surfaces of the fiber material and improve the mouthfeel characteristics thereof. Preferred temperatures and times are about 110 to 140° F. and about 100 to 240 minutes with a most preferred temperature and time of 120° F. and 120 minutes. As previously noted this degree of hydrolysis or modification is sufficient to smooth the surfaces of the soy fiber material and improve its sensory properties including mouthfeel characteristics and smoothness but without substantially reducing the dietary fiber content of the material itself. In this regard, the present procedure for modifying the soy fiber material only reduces the total dietary fiber level to not more than 10% by weight on a dry basis and usually about 2–10% by weight. The total dietary fiber content is intended to refer to the dietary fiber content which is measured by the procedure described in J.A.O.A.C., 68(2): 399 (1985).

Following the modification of the dietary fiber material the aqueous slurry is neutralized usually at a pH of about 6.5 to 7.0 by the addition of a suitable alkali such as sodium hydroxide. The neutralized slurry is then jet cooked to inactivate the enzyme. Jet cooking of soy protein or similar materials is a well recognized procedure and is generally described in U.S. Pat. Nos. 3,694,221 and 3,642,490 (herein incorporated by reference). Jet cooking of protein materials and the like consists of heating a neutralized slurry of the protein dynamically under positive pressure for a relatively short period of time and then expelling the heated slurry into an area of reduced atmospheric pressure. Although the present invention is not intended to be limited by the pressures and temperatures, or times used in the jet cooking step, nevertheless typical temperatures exceed 300° F. and the time the slurry is held under positive pressure usually exceeds about 5 seconds, typically 7–12 seconds. The jet cooked or enzyme inactivated slurry is then dewatered or dried preferably by spray drying.

The following Examples are intended to provide and disclose specific embodiments of the present invention.

EXAMPLE 1

Approximately 700 gallons of soy spent flakes having a total solids content of 4.2% by weight was adjusted to a pH of 4.53 by the addition of 2250 ml of phosphoric acid (85% by weight). The spent flake slurry was then concentrated to a total solids level of 14.9% by weight and maintained at a temperature of 48° F.

To serve as a control for the sensory experiments conducted below approximately 160 lb of the above slurry was diluted to a total solids content of 7.52% by the addition of water. The pH of the slurry was adjusted to a pH of 6.8 by the addition of 60 ml of a 50% sodium hydroxide solution. This slurry was then jet cooked at a temperature of 305° F. under positive pressure for a period of 9 seconds. The jet cooked slurry was then spray dried to provide an unmodified control for the sensory evaluation.

One hundred forty-six pounds of the slurry having a total solids level of 7.52% by weight and a pH of 4.0 was modified by the addition of a combination of 1 part by weight of a cellulase identified as Celluclast 1.5L available from (Novo Nordisk Bioindustrial, Inc., Danbury, Conn.) having an activity of 1500 NCU/g and 3 parts by weight of a carbohydrase identified a "Viscozyme L" having an activity of 120 fungal beta glucanase units/ml available from (Novo Nordisk Bioindustrial, Inc., Danbury, Conn.). The enzyme mixture was added in an amount of 2% by weight of the total solids level of the slurry. Modification was carried out by reaction with the enzyme mixture at a temperature of 122°±10° F. for 60 or 120 minutes. After 60 minutes 150 lb of modified fiber slurry was removed from the reaction tank, neutralized to a pH of 6.7 by the addition of 80 ml of 50% sodium hydroxide solution. The slurry was jet cooked at a temperature of about 305° F. under positive pressure for about 9 seconds and then spray dried to produce a modified soy fiber material.

Following almost 120 minutes of hydrolysis another 150 lb of fiber slurry was removed from the reaction tank, neutralized, jet cooked and dried as described above. The two modified soy fiber samples, together with two samples of the unmodified control were then analyzed and evaluated for sensory properties, chalkiness or mouthfeel. The results including the total dietary content of the samples are set forth in Table 1 below.

TABLE 1

| | Viscosity at 6% Centipoise | Protein | Ash | Sensory Chalkiness | Total dietary Fiber |
|---|---|---|---|---|---|
| Unmodified Soy Fiber # 1 | 1175 | 20.6 | 5.8 | 7.5 | 66.8 |
| Unmodified Soy Fiber # 2 | 1050 | 20.7 | 5.6 | 8.3 | 70.1 |
| Modified Soy Fiber (60 min) | 650 | 20.3 | 5.3 | 2.2 | 64.8 |
| Modified Soy Fiber (120 min) | 600 | 20.7 | 5.6 | 2.7 | 60.2 |

\* 1 = Not Chalky
10 = Very Chalky

A sensory evaluation of the above samples of soy fiber was also made by dispersal of each sample in skim milk at a level sufficient to provide a total dietary fiber level in an 8 oz serving of 5 grams. The results of this evaluation are set forth in Table 2.

TABLE 2

Sensory Evaluation in Skim Milk
5g/TDF per 8 oz Serving

| Product | Fiber solid (g) | * Mouthfeel Chalkiness |
|---|---|---|
| Unmodified Soy Fiber # 1 | 7.1 | 9.6 |
| Unmodified Soy Fiber # 2 | 7.0 | 9.4 |
| Modified Soy Fiber (60 min) | 7.7 | 2.3 |
| Modified Soy Fiber (120 min) | 8.3 | 2.7 |

\* Mouthfeel
1 = Not Chalky
10 = Very Chalky

It may be seen from the above data that the sensory properties of the soy fiber have been considerably improved by modification, but without a significant reduction in total dietary fiber content.

EXAMPLE 2

A modified dietary soy fiber material was produced by diluting a slurry of cleaned spent soy flakes to a total solids level of 7.59% with water. The pH of the slurry was adjusted to a pH of about 4. This was followed with the addition of 2% by weight of the total solids level of the slurry of the enzyme mixture described in Example 1. Hydrolysis was carried out at a temperature of about 110° F. for about 90 minutes after which the pH of the slurry was adjusted to a pH of 6.75 with Sodium Hydroxide solution.

The slurry was jet cooked at 305° F. under positive pressure for about 9 seconds and then spray dried.

The product was evaluated and analyzed as described in Table 3 below.

TABLE 3

| Product | Viscosity at 6% CPS | Sensory Chalkiness | Dietary Fiber % Total | Insoluble | Soluble |
|---|---|---|---|---|---|
| Modified Soy fiber (90 min) | 235 | 2.5 | 68.8 | 65.5 | 3.3 |

\* Chalkiness
1 = Not Chalky
10 = Very Chalky

It may be seen that the sensory properties of the product was desirable without a significant reduction in dietary fiber level.

EXAMPLE 3

In order to compare the sensory properties achieved using the enzyme system of the present invention with the combination of a cellulase and pectinase described in *Lebensmittel-wiessenchaft and Technologies* 20, p. 245–250 (1987), the following experiment was conducted.

Three hundred and ninety pounds (390 lbs) of spent flake slurry produced as described in Example 1 was adjusted to a solids level of about 7% by weight by the addition of water. The pH or the slurry was adjusted to about 4.0 by the addition of acid. One portion of the slurry was treated with the one part of a cellulase and three parts of a carbohydrase as described in Example 1, at a temperature of 122° F. for 120 min. A second portion of the slurry was treated with 0.5% "Celluclast" and 0.3% Pectinase based upon the % of fiber solids, and was reacted with this enzyme combination for 120 rain at a temperature of 122° F. The pH of each treated slurry was adjusted to a pH of 6.7 by the addition of sodium hydroxide and treated to a temperature of 180° F. by the addition of steam to inactivate the enzymes. Each portion was jet cooked as described in Example 1 and spray dried. Each portion was analyzed and evaluated for sensory properties as generally described in Example 1. The results are listed in Table 3 below.

TABLE 4

| | Total Dietary Fiber | *Mouthfeel Chalkiness |
|---|---|---|
| Present Invention | 73.45 | 2.50 |
| Cellulose/Pectinase | 78.45 | 4.01 |

\*1 = Not Chalky
10 = Very Chalky

It may be seen that the emzymatic combination used to treat the spent flakes pursuant to the present invention improved the sensory properties of the fiber.

The above Examples disclose specific embodiments of the present invention and it is intended hereby to include within the scope of the present invention all reasonable equivalents, variations and additions thereto.

We claim:

1. A process for the production, from unmodified soy dietary fiber, of a modified soy dietary fiber material of improved sensory properties of smoothness and mouthfeel compared to the unmodified soy dietary fiber, comprising:

a. forming an aqueous slurry of unmodified soy dietary fiber material having exposed surfaces;

b. enzymatically modifying the slurry of soy fiber with an enzyme mixture of a cellulase and carbohydrase material for a time sufficient to smooth said exposed surfaces and thereby improve said sensory properties of smoothness and mouthfeel of the soy fiber but without a reduction greater than about 10% by weight in the total dietary fiber content of the modified soy fiber material.

2. The process of claim 1 wherein the aqueous slurry has a total solids level of about 6 to 9% by weight.

3. The process of claim 1 wherein the aqueous slurry has a pH of about 3.75 to 4.25.

4. The process of claim 1 wherein the aqueous slurry has a temperature of about 120°–140° F.

5. The process of claim 1 wherein the cellulase is derived from *Trichoderma longbrachiatum*.

6. The process of claim 1 wherein the carbohydrase comprises a mixture of arabinases, cellulases beta glucanases, hemicellulases, and xylanases.

7. An enzymatically modified soy dietary fiber made according to the process set forth in claim 1.

8. The process of claim 1 wherein the enzyme mixture comprises by weight about 1 part cellulase and about 3 parts carbohydrase.

9. An enzymatically modified soy dietary fiber made according to the process set forth in claim 8.

10. The process of claim 1 wherein the enzymatically modified slurry is dewatered.

11. The process of claim 10 wherein pH of the enzymatically modified slurry is adjusted to about 6.5–7.0 before dewatering.

12. The process of claim 10 wherein dewatering is carried out by spray drying.

13. The process of claim 1 including the step of jet cooking the enzymatically modified slurry.

14. The process of claim 13 wherein the aqueous slurry has a pH of about 3.75–4.25.

15. The process of claim 13 wherein the aqueous slurry has a temperature of about 120°–140° F.

16. The process of claim 13 wherein the aqueous slurry has a total solids level of about 6–9% by weight.

17. The process of claim 16 wherein the aqueous slurry is adjusted to a pH of about 6.5–7.0.

18. A process for the production, from unmodified soy dietary fiber, of a modified soy dietary fiber material of improved sensory properties including mouthfeel characteristics and smoothness compared to the unmodified soy dietary fiber, comprising:

a. forming an aqueous slurry of an unmodified soy fiber material having exposed surfaces;

b. enzymatically hydrolyzing the slurry of soy fiber with an enzyme mixture comprising in parts by weight about 1 part cellulase and about 3 parts carbohydrase for a time sufficient to smooth said exposed surfaces; and c. jet cooking the hydrolyzed slurry of soy fiber followed by dewatering thereof.

19. The process of claim 18 wherein the hydrolyzed slurry is adjusted to about a neutral pH prior to jet cooking.

20. The process of claim 18 wherein jet cooking is carried out at a temperature of at least 300° F., and is retained under a positive pressure for at least about 7 seconds.

21. An enzymatically modified soy dietary fiber made according to the process set forth in claim 18.

22. The process of claim 18 wherein the cellulase is derived from *Trichoderma longbrachiatum*.

23. The process of claim 22 wherein the carbohydrase comprises a mixture of arabinases, cellulases, beta glucanases, hemicellulases, and xylanases.

24. An enzymatically modified soy dietary fiber made according to the process set forth in claim 23.

* * * * *